(12) United States Patent
Grubis et al.

(10) Patent No.: US 8,310,374 B2
(45) Date of Patent: Nov. 13, 2012

(54) TELEMETRY SYSTEM AND METHOD

(75) Inventors: Mathew George Grubis, New Berlin, WI (US); Bruce Arnold Friedman, Jasper, GA (US); Robert Joseph Alberte, Jr., Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 617 days.

(21) Appl. No.: 12/397,789

(22) Filed: Mar. 4, 2009

(65) Prior Publication Data
US 2010/0225501 A1  Sep. 9, 2010

(51) Int. Cl.
G08B 21/00 (2006.01)
G08C 19/00 (2006.01)

(52) U.S. Cl. .......... 340/870.16; 340/870.01; 340/870.03
(58) Field of Classification Search .............. 340/573.1, 340/539, 572.1, 870.07
See application file for complete search history.

(56) References Cited

U.S. PATENT DOCUMENTS

| | | | |
|---|---|---|---|
| 4,275,385 A | 6/1981 | White | |
| 4,814,751 A * | 3/1989 | Hawkins et al. | 340/573.1 |
| 5,396,224 A | 3/1995 | Dukes et al. | |
| 6,084,513 A * | 7/2000 | Stoffer | 340/572.2 |
| 6,144,303 A * | 11/2000 | Federman | 340/573.4 |
| 6,225,906 B1 * | 5/2001 | Shore | 340/573.4 |
| 6,259,355 B1 * | 7/2001 | Chaco et al. | 340/286.07 |
| 6,510,344 B1 | 1/2003 | Halpern | |
| 6,544,174 B2 * | 4/2003 | West et al. | 600/300 |
| 7,242,306 B2 | 7/2007 | Wildman et al. | |
| 7,248,933 B2 | 7/2007 | Wildman | |
| 7,277,714 B1 | 10/2007 | Mikan et al. | |
| 7,321,862 B2 | 1/2008 | Rosenfeld et al. | |
| 7,429,243 B2 | 9/2008 | KenKnight et al. | |
| 2002/0060630 A1 * | 5/2002 | Power | 340/573.1 |
| 2003/0146835 A1 | 8/2003 | Carter | |
| 2005/0035862 A1 | 2/2005 | Wildman et al. | |
| 2005/0073419 A1 * | 4/2005 | Gary, Jr. | 340/573.1 |
| 2006/0155584 A1 * | 7/2006 | Aggarwal | 705/3 |
| 2006/0176149 A1 | 8/2006 | Douglas | |

(Continued)

FOREIGN PATENT DOCUMENTS
WO   2007069890   6/2007

OTHER PUBLICATIONS

Leonhardi et al., "A map-based dead reckoning protocol for updating location information", Proceedings of International Parallel and Distributed Processing Symposium, 2002, 193-200.

(Continued)

Primary Examiner — Rexford Barnie
Assistant Examiner — Angela Brooks
(74) Attorney, Agent, or Firm — Andrus, Sceales, Starke & Sawall, LLP

(57) ABSTRACT

A telemetry system is disclosed herein. The telemetry system includes a transmitter/monitor configured to provide tracking data and monitoring data, and a receiver adapted to define a coverage area. The receiver is configured to receive the tracking data and the monitoring data from the transmitter/monitor when the transmitter/monitor is within the coverage area. The telemetry system also includes a processor configured to receive the tracking data and the monitoring data from the receiver, analyze the tracking data and the monitoring data, and identify an alarm condition based on the analysis of the tracking data and the monitoring data.

22 Claims, 3 Drawing Sheets

U.S. PATENT DOCUMENTS

| | | |
|---|---|---|
| 2006/0206011 A1 | 9/2006 | Higgins et al. |
| 2006/0226974 A1 | 10/2006 | Fluegel |
| 2006/0250234 A1 | 11/2006 | Maschke |
| 2007/0080801 A1 | 4/2007 | Weismiller et al. |
| 2007/0096897 A1 | 5/2007 | Weiner |
| 2008/0048914 A1 | 2/2008 | Smith et al. |
| 2008/0094208 A1 | 4/2008 | Schwartz |
| 2008/0246629 A1* | 10/2008 | Tsui et al. ............... 340/870.07 |
| 2008/0275307 A1 | 11/2008 | Poschmann |
| 2009/0273455 A1 | 11/2009 | Sweeney et al. |

OTHER PUBLICATIONS

Zhu et al., "The principle of non-sensor dead reckoning", Geoscience and Remote Sensing Symposium, Jul. 25, 2005, 4693-4696.

Notice of Allowance issued Mar. 5, 2012, in connection with U.S. Appl. No. 12/397,710.

* cited by examiner

TELEMETRY SYSTEM AND METHOD

FIELD OF THE INVENTION

This disclosure relates generally to a telemetry system and associated method.

BACKGROUND OF THE INVENTION

Telemetry systems can be implemented to acquire and transmit data from a remote source. The telemetry system may incorporate a wireless technology such as wireless fidelity (WiFi); infrared (IR); or ultrasound in order to facilitate finding an object and/or data transmission. As an exemplary implementation, a medical telemetry system can be implemented to remotely monitor the cardiac electrical activity of a plurality of ambulatory patients while they remain within a predefined coverage area. The medical telemetry system may also be implemented to locate and track patients within the coverage area.

Medical telemetry systems may comprise an alarm adapted to identify high risk patients and/or patients requiring special assistance. Some medical procedures and diagnostic examinations require the removal of any telemetry system components attached directly to a patient. One problem with conventional medical telemetry systems is that the process of removing telemetry system components for purposes of performing a medical procedure or diagnostic examination can generate a false alarm. False alarms unnecessarily tax hospital resources and interfere with the working environment.

BRIEF DESCRIPTION OF THE INVENTION

The above-mentioned shortcomings, disadvantages and problems are addressed herein which will be understood by reading and understanding the following specification.

In an embodiment, a telemetry system includes a transmitter/monitor configured to provide tracking data and monitoring data, and a receiver adapted to define a coverage area. The receiver is configured to receive the tracking data and the monitoring data from the transmitter/monitor when the transmitter/monitor is within the coverage area. The telemetry system also includes a processor configured to receive the tracking data and the monitoring data from the receiver, analyze the tracking data and the monitoring data, and identify an alarm condition based on the analysis of the tracking data and the monitoring data.

In another embodiment, a telemetry system includes a portable transmitter/monitor configured to provide tracking data and monitoring data, and a receiver network adapted to define a coverage area. The receiver network is configured to receive the tracking data and the monitoring data from the portable transmitter/monitor when the portable transmitter/monitor is within the coverage area. The telemetry system also includes a processor configured to receive the tracking data and the monitoring data from the receiver. The processor is further configured to identify a false alarm region disposed within the coverage area; identify an alarm condition based on the monitoring data; and cancel the alarm condition if the tracking data indicates that the portable transmitter/monitor is within the false alarm region.

In another embodiment, a method includes providing a telemetry system comprising a transmitter/monitor configured to provide tracking data and monitoring data, and a receiver adapted to define a coverage area. The receiver is configured to receive the tracking data and the monitoring data from the transmitter/monitor when the transmitter/monitor is within the coverage area. The method also includes identifying a false alarm region disposed within the coverage area, identifying an alarm condition based on the monitoring data, and canceling the alarm condition if the tracking data indicates that the transmitter/monitor is within the false alarm region.

In another embodiment, a telemetry system includes a transmitter/monitor configured to provide tracking data. The transmitter/monitor includes an alarm shutoff feature. The transmitter/monitor also includes a receiver adapted to define a coverage area. The receiver is configured to receive the tracking data from the transmitter/monitor when the transmitter/monitor is within the coverage area. The transmitter/monitor also includes a processor configured to receive the tracking data from the receiver; to identify a false alarm region within the coverage area; and to regulate the status of the alarm shutoff feature based on the false alarm region and the patient tracking data.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
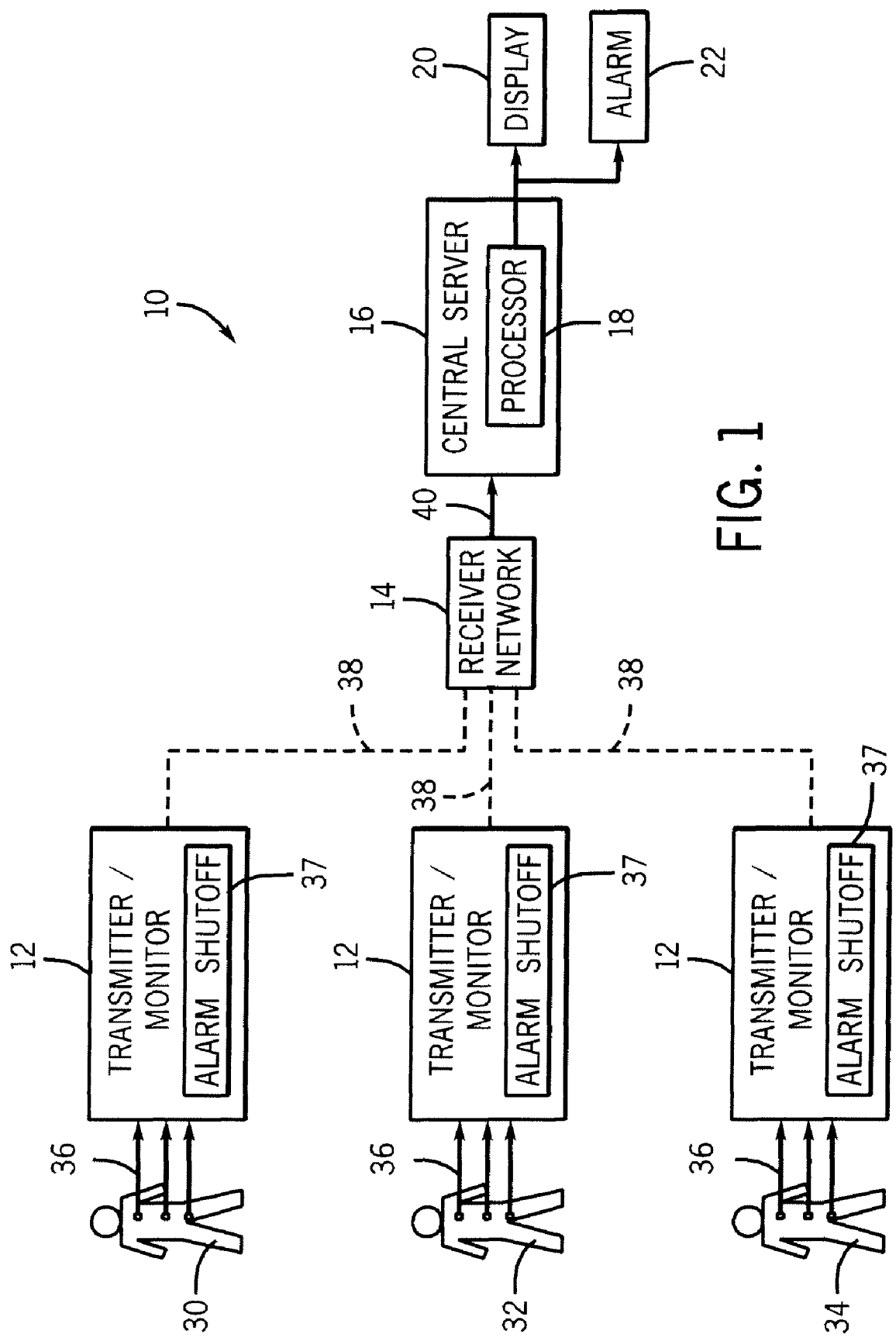
FIG. 1 is a schematic representation of a telemetry system in accordance with an embodiment.

Referring to FIG. 1, a telemetry system 10 is shown in accordance with an embodiment. The telemetry system 10 includes one or more transmitter/monitors 12; one or more receivers 14; and a central server 16 comprising a processor 18. The telemetry system 10 may also optionally include a display 20; and an alarm 22. Those skilled in the art will appreciate that the telemetry system 10 is configured to track the relative location of the transmitter/monitors 12, and that a transmitter/monitor 12 can be assigned to a specific patient in order to track and/or monitor that patient. For illustrative purposes assume that three patients 30-34 are being tracked and monitored by the telemetry system 10. It should, however, be appreciated that the telemetry system 10 may be implemented to track and/or monitor a much larger number of patients.

The transmitter/monitors 12 will be described in accordance with an embodiment as a portable device comprising an electrocardiograph and a plurality of electrocardiograph sensors 36 configured to monitor cardiac electrical activity. For purposes of this disclosure, a portable device should be defined to include any device that is sufficiently compact and lightweight such that a typical patient can conveniently carry the device wherever they go. Each transmitter/monitors 12 may optionally include an alarm shutoff feature 37 described in detail hereinafter.

A separate transmitter/monitor 12 is assigned to each of the patients 30-34, and thereafter the assigned transmitter/monitor 12 generates patient monitoring data and/or patient tracking data. For purposes of this disclosure, the term patient monitoring data is defined to include data acquired during the process of monitoring or evaluating a predefined characteristic. According to the illustrative embodiment wherein the transmitter/monitors 12 comprise an electrocardiograph, the patient monitoring data may include cardiac electrical activity data. Also for purposes of this disclosure, the term patient tracking data is defined to include data identifying a given patient's location. The patient monitoring data and/or patient tracking data from the transmitter/monitors 12 is transferred to the receivers 14 via the wireless connections 38 represented by a dashed line.

The receiver 14 will be described in accordance with an embodiment as comprising a network of receivers 14 that are uniformly distributed throughout a region of interest in order to define a coverage area. The region of interest may, for example, include an area with a high-patient density such as a patient ward. The network of receivers 14 transfers the patient monitoring data and/or patient tracking data to the central server 16 via connection 40.

The central server 16 comprises the processor 18 configured to process the patient monitoring data and/or patient tracking data in a known manner. For example, the processor 18 may convert raw patient monitoring data acquired by the sensors 36 into more conveniently readable electrocardiogram (ECG) data comprising a P-wave, a QRS complex and a T-wave. The processor 18 may also be implemented to evaluate a potential alarm condition based on the corresponding patient's location within a coverage area in order to minimize false alarms.

The display 20 may be implemented to graphically convey patient monitoring data and/or patient tracking data from the central server 16 in a conveniently readable manner. As one example, the patient monitoring data may be graphically conveyed as a conventional ECG plot comprising a sequence of P-waves, a QRS complexes and a T-waves. As another example, the patient tracking data may be graphically conveyed as an icon superimposed onto a map to indicate the patient's relative location.

The alarm 22 may be implemented to alert hospital personnel when a patient has exited or is about to exit a given coverage area. The alarm 22 may comprise an audible device (e.g., a loudspeaker) and/or a visual device (e.g., a flashing light). The alarm 22 may be triggered by the processor 18 in response to an identified alarm condition described in more detail hereinafter.

Having described the components of the telemetry system 10 in detail, a method 100 (shown in FIG. 3) for predicting the location of a patient (or a transmitter/monitor 12 associated therewith) outside a coverage area will now be described with respect to FIGS. 2 and 3.

Figure 2:
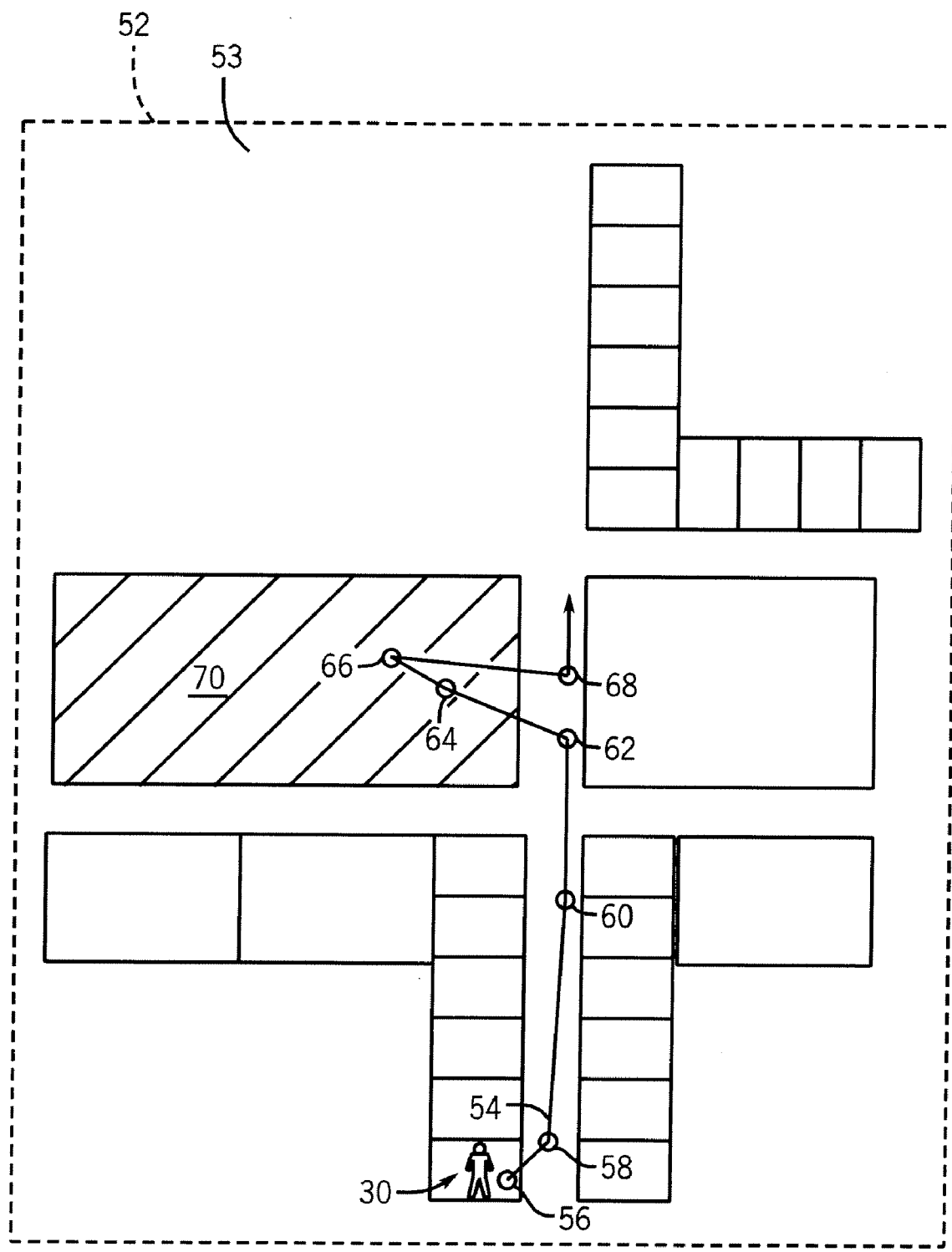
FIG. 2 is a schematic representation of a hospital map in accordance with an embodiment.

Referring to FIG. 2, a schematic representation of a hospital map 50 is shown in accordance with an embodiment. The region circumscribed by the dashed line 52 represents a coverage area 53 that may be defined by the receiver network 14 (shown in FIG. 1). As previously described, any patient having a transmitter/monitor 12 (shown in FIG. 1) can be tracked and monitored as long as they remain within the coverage area 53.

A solid line represents the path 54 of the patient 30 walking within the coverage area 53. Positions 56-68 are known positions along the patient's path 54. The crosshatched region of the map 50 represents a false alarm region 70 that is described in more detail hereinafter.

Figure 3:
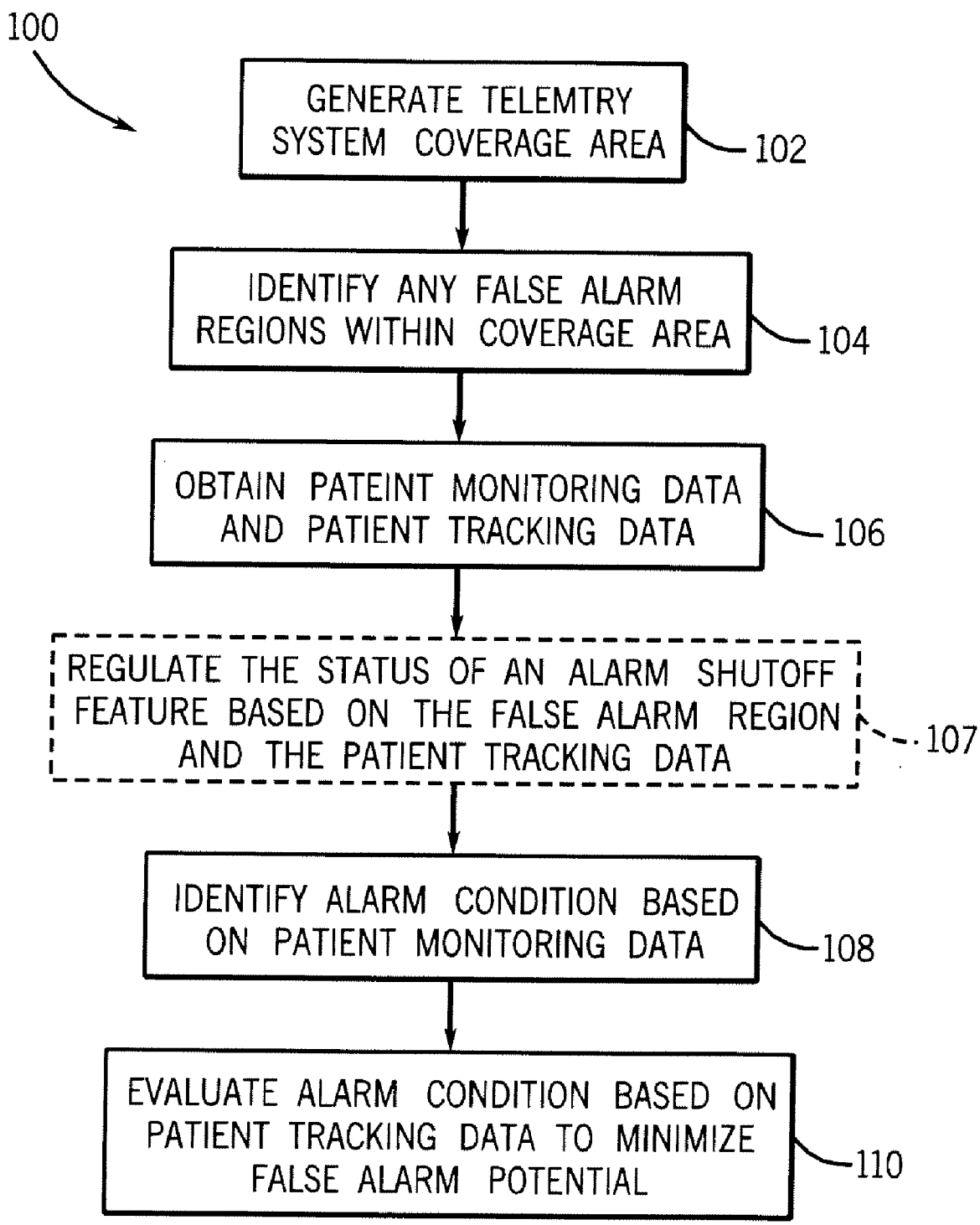
FIG. 3 is a flow chart illustrating a method in accordance with an embodiment.

Referring to FIG. 3, the method 100 will now be described in accordance with an embodiment. The method 100 comprises a plurality of steps 102-110. One or more of the steps 102-110 may be performed by the processor 18 (shown in FIG. 1). Referring now to both FIGS. 2 and 3, the method 100 will be described as it applies to the exemplary embodiment of FIG. 2 in order to more clearly illustrate the steps 102-110.

At step 102 the method 100 generates a telemetry system coverage area such as, for example, the coverage area 53. The coverage area 53 may be generated by uniformly distributing each receiver in the receiver network 14 (shown in FIG. 1) throughout a region of interest.

At step 104, the method 100 identifies any false alarm regions (e.g., the false alarm region 70) within the coverage area 53. The false alarm region may include any region associated with a high incidence of false alarms.

According to one embodiment, the false alarm region of step 104 may include a region in which the transmitter/monitor 12 (shown in FIG. 1) is likely to be disconnected from the patient for purposes of conducting a medical procedure or diagnostic examination. It should be appreciated that the removal of the transmitter/monitor 12 within the coverage area 53 interrupts the transfer of the signal from the sensors 36 (shown in FIG. 1) to the processor 18 (shown in FIG. 1), and could therefore produce a false alarm based on the incorrect assumption that the electrocardiograph leads have failed. Accordingly, by designating the false alarm region 70 in the manner described herein, the method 100 eliminates the false alarm that would otherwise be generated when patient 30 removes the transmitter/monitor 12 within the coverage area 53 for purposes of conducting a medical procedure or diagnostic examination. A non-limiting list of regions in which the transmitter/monitor 12 is likely to be disconnected from the patient for purposes of conducting a medical procedure or diagnostic examination may include any room in which X-rays; endoscopies; CT scans; MRIs; and/or PET scans are obtained.

According to another embodiment, the false alarm region of step 104 may include a region in which technological limitations may interfere with the operation of the telemetry system 10 (shown in FIG. 1). As an example, a technological limitation that interrupts the transfer of the signal from the transmitter/monitor 12 (shown in FIG. 1) to the receiver network 14 (shown in FIG. 1) could produce a false alarm based on the incorrect assumption that the electrocardiograph leads have failed. Accordingly, by designating the false alarm region 70 in the manner described herein, the method 100 eliminates the false alarm that would otherwise be generated when a technological limitation interferes with the operation of the telemetry system 10. A non-limiting example of a region in which technological limitations may interfere with the operation of the telemetry system 10 includes an elevator.

At step 106 the method 100 obtains patient monitoring data and patient tracking data from the transmitter/monitor 12 (shown in FIG. 1) while the patient 30 is within the coverage area 53. For illustrative purposes, assume the patient tracking data comprises the positions 56-68 acquired along path 54. According to one embodiment, the positions 56-68 are established by the processor 18 (shown in FIG. 1) based on patient tracking data.

Step 107 is an optional step in which the method 100 regulates the status of the alarm shutoff feature 37 of a transmitter/monitor 12 (shown in FIG. 1) based on the false alarm region of step 104 and the patient tracking data from step 106.

If, for example, the patient location data indicates that the patient is outside a false alarm region, the processor 18 (shown in FIG. 1) may automatically disable the alarm shutoff feature 37. Similarly, if the patient location data indicates that the patient is within a false alarm region, the processor 18 may automatically enable the alarm shutoff feature 37. Automatically enabling the alarm shutoff feature 37 when the patient is within a false alarm region allows a clinician to manually shut off the alarm associated with the patient's transmitter/monitor 12 to thereby avoid a potential false alarm. It should be appreciated that by enabling the alarm shutoff feature 37 only within a false alarm region patients are less likely to inadvertently shut off their own alarm.

At step 108 the method 100 identifies an alarm condition based on the patient monitoring data from the transmitter/monitor 12 (shown in FIG. 1). According to one embodiment, step 108 may be performed by implementing the processor 18 (shown in FIG. 1) to evaluate the patient monitoring data and thereby identify a potential alarm condition. As one example, the processor 18 may identify an alarm condition when the signal from the sensors 36 is lost such as, for example, when the sensors 36 fail or are removed from the patient. As another example, the processor 18 may identify an alarm condition based on an analysis of the signal from the sensors 36 such as, for example, an analysis of a QT-interval or a PQRST waveform morphology.

At step 110 the method 100 evaluates any identified alarm condition based on the patient tracking data from the transmitter/monitor 12 (shown in FIG. 1) in order to minimize false alarms. According to one embodiment, step 110 may be performed by implementing the processor 18 (shown in FIG. 1) to identify a current patient location based on the patient tracking data from the transmitter/monitor 12, and to cancel an identified alarm condition if the patient is within a false alarm region. Referring again to the example of FIG. 2, if an alarm condition associated with patient 30 is generated while patient 30 is in the false alarm region 70 (e.g., at positions 64 or 66), the alarm condition can be overridden based on the assumption that the patient's transmitter/monitor 12 has been intentionally removed for purposes of obtaining an X-ray. The elimination of false alarms in the manner described allows for a more optimal utilization of hospital resources, less alarm fatigue and provides an improved work environment with fewer interruptions.

Steps 108 and 110 of the method 100 have been described separately in accordance with an embodiment. It should be appreciated that steps 108 and 110 may alternatively be combined into a single step wherein an alarm condition is identified based on both patient monitoring data and patient tracking. As an example, the processor 18 may be implemented to identify an alarm condition if the signal from the sensors 36 is lost, the patient 30 is within the coverage area 53, and the patient 30 is outside the false alarm region 70.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A telemetry system comprising:
a transmitter/monitor configured to provide tracking data and monitoring data;
a receiver adapted to define a coverage area, said receiver configured to receive the tracking data and the monitoring data from the transmitter/monitor when the transmitter/monitor is within the coverage area; and
a processor configured to receive the tracking data and the monitoring data from the receiver, said processor further configured to analyze the tracking data and the monitoring data received when the transmitter is within the coverage area; and to identify an alarm condition based on the analysis of the tracking data and the monitoring data received when the transmitter is within the coverage area, and the processor further configured to trigger an alarm shut off in the tracking data indicates that the transmitter/monitor is in a false alarm region.

2. The telemetry system of claim 1, wherein the transmitter/monitor comprises an electrocardioghraph.

3. The telemetry system of claim 1, wherein the transmitter/monitor comprises a portable device that is adapted for attachment to a patient.

4. The telemetry system of claim 3, wherein the processor is configured to identify a false alarm region within the coverage area.

5. The telemetry system of claim 4, wherein the false alarm region is a predefined region in which the transmitter/monitor is likely to be disconnected from the patient for purposes of conducting a medical procedure or diagnostic examination.

6. The telemetry system of claim 4, wherein the false alarm region comprises a predefined region in which X-rays; endoscopies; CT scans; MRIs; and/or PET scans are obtained.

7. The telemetry system of claim 4, wherein the false alarm region comprises a predefined region in which technological limitations may interfere with the operation of the telemetry system.

8. The telemetry system of claim 4, wherein the processor is configured to identify the alarm condition only if the transmitter/monitor is within the coverage area and outside the false alarm region.

9. The telemetry system of claim 1, further comprising an alarm connected to the processor, said alarm configured to generate a visual and/or audible warning in response to the identified alarm condition.

10. A telemetry system comprising:
a portable transmitter/monitor configured to provide tracking data and monitoring data;
a receiver network adapted to define a coverage area, said receiver network configured to receive the tracking data and the monitoring data from the portable transmitter/monitor when the portable transmitter/monitor is within the coverage area; and
a processor configured to receive the tracking data and the monitoring data from the receiver network, said processor further configured to identify a false alarm region disposed within the coverage area; identify an alarm condition based on the monitoring data received when the transmitter is within the coverage area; and cancel the alarm condition if the tracking data received when the transmitter is within the coverage area indicates that the portable transmitter/monitor is within the false alarm region.

11. The telemetry system of claim 10, wherein the portable transmitter/monitor comprises an electrocardiograph.

12. The telemetry system of claim 10, wherein the false alarm region is a predefined region in which the portable transmitter/monitor is likely to be disconnected from a patient for purposes of conducting a medical procedure of diagnostic examination.

13. The telemetry system of claim 10, wherein the false alarm region comprises a predefined region in which X-rays; endoscopies; CT scans; MRIs; and/or PET scans are obtained.

14. The telemetry system of claim 10, wherein the false alarm region comprises a predefined region in which technological limitations may interfere with the operation of the telemetry system.

15. The telemetry system of claim 10, further comprising an alarm connected to the processor, said alarm configured to generate a visual and/or audible warning in response to the identified alarm condition.

16. A method comprising;
providing a telemetry system comprising:
   a transmitter/monitor configured to provide tracking data and monitoring data; and
   a receiver adapted to define a coverage area, said receiver configured to receive the tracking data and the monitoring data from the transmitter/monitor when the transmitter/monitor is within the coverage area;
identifying a false alarm region disposed within the coverage area;
identifying an alarm condition based on the monitoring data received when the transmitter is within the coverage area; and
canceling the alarm condition if the tracking data received when the transmitter is within the coverage area indicates that the transmitter/monitor is within the false alarm region.

17. The method of claim 16, wherein said identifying a false alarm region comprises identifying a region in which the transmitter/monitor is likely to be disconnected from a patient for purposes of conducting a medical procedure or diagnostic examination.

18. The method of claim 16, wherein said identifying a false alarm region comprises identifying a region in which X-rays; endoscopies; CT scans; MRIs; and/or PET scans are obtained.

19. The method of claim 16, further comprising generating a visual and/or audible warning in response to the alarm condition.

20. A telemetry system comprising:
   a transmitter/monitor configured to provide tracking data, said transmitter/monitor comprising an alarm shutoff feature;
   a receiver adapted to define a coverage area, said receiver configured to receive the tracking data from the transmitter/monitor when the transmitter/monitor is within the coverage area; and
   a processor configured to receive the tracking data from the receiver, said processor further configured to identify a false alarm region within the coverage area; and to regulate the status of the alarm shutoff feature based on the false alarm region and the patient tracking data received when the transmitter is within the coverage area.

21. The telemetry system of claim 20, wherein the false alarm region is a predefined region in which the transmitter/monitor is likely to be disconnected from the patient for purposes of conducting a medical procedure or diagnostic examination.

22. The telemetry system of claim 20, wherein the false alarm region comprises a predefined region in which technological limitations may interfere with the operation of the telemetry system.

* * * * *